(12) United States Patent
Kataoka et al.

(10) Patent No.: US 8,153,110 B2
(45) Date of Patent: Apr. 10, 2012

(54) ENVIRONMENT-RESPONDING SIRNA CARRIER USING DISULFIDE-CROSS-LINKED POLYMERIC MICELLE

(75) Inventors: Kazunori Kataoka, Tokyo (JP); Nobuhiro Nishiyama, Tokyo (JP); Satoru Matsumoto, Tokyo (JP)

(73) Assignee: The University of Tokyo, Tokyo (JP)

( * ) Notice: Subject to any disclaimer, the term of this patent is extended or adjusted under 35 U.S.C. 154(b) by 0 days.

(21) Appl. No.: 12/515,464

(22) PCT Filed: Nov. 22, 2007

(86) PCT No.: PCT/JP2007/073130
§ 371 (c)(1),
(2), (4) Date: Dec. 29, 2009

(87) PCT Pub. No.: WO2008/062909
PCT Pub. Date: May 29, 2008

(65) Prior Publication Data
US 2010/0121043 A1 May 13, 2010

(30) Foreign Application Priority Data
Nov. 22, 2006 (JP) ................................ 2006-315753

(51) Int. Cl.
*A61K 47/48* (2006.01)
*A61K 9/14* (2006.01)
*C07H 21/02* (2006.01)

(52) U.S. Cl. ..................... 424/78.17; 424/486; 536/24.5

(58) Field of Classification Search ......................... None
See application file for complete search history.

(56) References Cited

U.S. PATENT DOCUMENTS
7,056,704 B2 * 6/2006 Tuschl et al. ................. 435/91.1

FOREIGN PATENT DOCUMENTS
| WO | 96/33233 | 10/1996 |
| WO | 98/32434 | 10/1996 |
| WO | 97/06202 | 2/1997 |

OTHER PUBLICATIONS

Miyata, K., et al. "Block Catiomer Polyplexes with Regulated Densities of Charge and Disulfide Cross-Linking Directed to Enhance Gene Expression." J. Am. Chem. Soc. (2004) vol. 126, No. 8, pp. 2355-2361.

Read, M. L., et al. "A versatile reducible polycation-based system of efficient delivery of a broad range of nucleic acids." Nucleic Acids Research (2005) vol. 33, No. 9, e86, pp. 1-16.

Kakizawa, Y., et al. "Glutathione-Sensitive Stabilization of Block Copolymer Micelles Composed of Antisense DNA and Thiolated Poly(ethylene glycol)-block-poly(L-lysine): A Potential Carrier for Systemic Delivery of Antisense DNA." Biomacromolecules (2001) vol. 2, pp. 491-497.

Soundara, D., et al. "Polyplex gene delivery modulated by redox potential gradients." Journal of Drug Targeting (2006) vol. 14, No. 8, pp. 519-526.

Fire, A., et al. "Potent and specific genetic interference by double-stranded RNA in Caenorhabditis elegans" *Nature* (1998) vol. 391, pp. 806-811.

Elbashir, S. M., et al. "Duplexes of 21-nucleotide RNAs mediate RNA interference in cultured mammalian cells" *Nature* (2001) vol. 411, pp. 494-498.

Zimmermann, T. S., et al. "RNAi-mediated gene silencing in non-human primates" *Nature* (2006) vol. 441, pp. 111-114.

Yamauchi, M., et al. "Improved formulations of antisense oligodeoxynucleotides using wrapped liposomes." *Journal of Controlled Release* (2006) vol. 114, pp. 268-275.

Kataoka, K., et al. "Spontaneous Formation of Polyion Complex Micelles with Narrow Distribution from Antisense Oligonucleotide and Cationic Block Copolymer inn Physiological Saline" *Macromolecules* (1996) vol. 29, pp. 8556-8557.

Wolfert, M. A., et al. "Characterization of Vectors for Gene Therapy Formed by Self-Assembly of DNA with Synthetic Block Co-Polymers." *Human Gene Therapy* (1996) vol. 7, pp. 2123-2133.

Katayose, S., et al. "Water-Soluble Polyion Complex Associates of DNA and Poly(ethylene glycol)—Poly(L-lysine) Block Copolymer" *Bioconjugate Chem.* (1997) vol. 8, pp. 702-707.

Katayose, S., et al. "Remarkable Increase in Nuclease Resistance of Plasmid DNA through Supramolecular Assembly with Poly(ethylene glycol)-Poly(L-lysine) Block Copolymer" *Journal of Pharmaceutical Sciences* (1998) vol. 87, No. 2, pp. 160-163.

Itaka, Keiji, et al. "Polyion complex micelles from plasmid DNA and poly(ethylene glycol)poly(L-lysine) block copolymer as serum-tolerable polyplex system; physicochemical properties of micelles relevant to gene transfection efficiency" Biomaterials 24 (2003) 4495-4506.

Shimizu, Hideki, et al. "siRNA-Based Therapy Ameliorates Glomerulonephritis" J Am Soc Nephrol 21: 622-633, 2010. Mar. 4, 2010.

* cited by examiner

*Primary Examiner* — Richard Schnizer
(74) *Attorney, Agent, or Firm* — Ladas & Parry LLP

(57) ABSTRACT

Disclosed is a siRNA-encapsulating polymeric micelle complex (a polyion complex) having high monodispersibility and structural stability and excellent in the ability of transporting siRNA into a cell. Further disclosed are a nucleic acid delivery device, a nucleic acid delivery kit, a pharmaceutical composition, and a gene therapy agent, each of which uses the complex. The polyion complex is characterized by comprising: a block copolymer composed of a polyethylene glycol moiety and a polycation moiety having a thiol group as a side chain at the terminus; and siRNA.

12 Claims, 9 Drawing Sheets

Electrostatic interaction

SEQUENCE LISTING

<160> NUMBER OF SEQ ID NOS: 2

<210> SEQ ID NO 1
<211> LENGTH: 21
<212> TYPE: DNA
<213> ORGANISM: Artificial Sequence
<220> FEATURE:
<223> OTHER INFORMATION: DNA/RNA binding molecule

<400> SEQUENCE: 1
cuuacgcuga guacuucgat t                                          21

<210> SEQ ID NO 2
<211> LENGTH: 21
<212> TYPE: DNA
<213> ORGANISM: Artificial Sequence
<220> FEATURE:
<223> OTHER INFORMATION: DNA/RNA binding molecule

<400> SEQUENCE: 2
ucgaaguacu cagcguaagt t                                          21

ENVIRONMENT-RESPONDING SIRNA CARRIER USING DISULFIDE-CROSS-LINKED POLYMERIC MICELLE

TECHNICAL FIELD

The present invention relates to a polymer micelle complex containing a nucleic acid, and particularly relates to a polymer micelle complex containing siRNA. The present invention also relates to a nucleic acid delivery device, a nucleic acid delivery kit, a pharmaceutical composition and a gene therapy agent, each of which comprises the complex.

BACKGROUND ART siRNA (small interfering RNA) is a double-stranded RNA with 19 to 21 base pairs, and is a molecule playing a major role in RNA interference (RNAi), which is known as potent and specific gene expression suppression phenomenon (Fire A et al., Potent and specific genetic interference by double-stranded RNA in *Caenorhabditis elegans*, Nature, vol. 391, pp. 744-745, 1998). Since RNAi in mammalian cells was reported by Tushl et al. in 2001 (Sayda M et al., Duplexes of 21-nucleotide RNAs mediate RNA interference in cultured mammalian cells, Nature, vol. 411, pp. 494-498, 2001), research and development for the purpose of application of siRNA to every treatment of disease have been promoted. However, in the preceding development, sites in which affected areas can be easily reached, such as eyes and respiratory organs, have been targeted, and therefore the range of application is limited. siRNA is an unstable chemical species and is easily degraded under physiological circumstances. It is known that, when siRNA is solely administered intravenously to a mouse, it is excreted from kidney rapidly ($t_{1/2}$=several minutes). Therefore, DDS, which improves disposition of siRNA, is desired as a key to practical application of siRNA.

However, systemic DDS is still at the level of laboratory and miles away from practical application. Even in the case of the system of SNALP (Stable Nucleic Acid Lipid Particles) provided by Alnylam and Protiva Biotherapeutics, regarding which the most advanced achievement has been reported, it is difficult to apply the system to tissue other than liver tissue due to passive uptake into liver (Tracy S et al., RNAi-mediated gene silencing in non-human primates, Nature, vol. 441, pp. 111-114, 2006). Meanwhile, in terms of long-term retention in the blood, retentivity was successfully and dramatically improved by the system of Wrapped liposome provided by Kyowa Hakko, though single-stranded DNA was targeted by the system (Masahiro Yamauchi et al., Improved formulations of Antisense oligonucleotides using wrapped liposomes, J. Control Release, vol. 114, pp. 268-275, 2006), and future development regarding siRNA is particularly expected. However, in the case of liposome, it is often difficult to release an agent therein since it is too stable.

As described above, in order to extend the range of application of siRNA, it is extremely important to provide a technique for improving disposition of siRNA and allowing siRNA administration into the blood stream.

With respect to plasmid DNA and antisense DNA, nanometer-scale structures in which such a DNA is encapsulated using poly(ethylene glycol)-poly(L-lysine) block copolymer (PEG-PLys) (i.e., polymer micelles) have been formed, and their utility has been reported (K. Kataoka et al., Spontaneous formation of polyion complex micelles with narrow distribution form antisense oligonucleotide and cationic block copolymer in physiological saline, Macromolecules, vol. 29, pp. 8556-8557, 1996; M. A. Woflert et al., Characterization of vector for gene therapy formed by self-assembly of DNA with synthetic block co-polymers. Hum., Gene Ther., vol. 7, pp. 2123-2133, 1996; S. Katayose et al., Water-soluble polyion complex associates of DNA and poly(ethylene glycol)-poly (L-lysine) block copolymer. Bioconjug., Chem., vol. 8, pp. 702-707, 1997; S. Katayose et al., Remarkable increase in nuclease resistance of plasmid DNA through supramolecular assembly with poly(ethylene glycol)-poly(L-lysine) block copolymer, J. Pharm. Sci., vol. 87, pp. 160-163, 1998).

Such a polymer micelle is formed by self-assembly caused by electrostatic interaction between a polycation portion in the above-described block copolymer (a polylysine portion in PEG-PLys) and a polyanion, a nucleic acid molecule (DNA, etc.). The polymer micelle formed has a core-shell-type structure, in which the polyion complex portion between polycation and polyanion is an inner core-like portion, and the surface layer thereof is like being covered with polyethylene glycol (PEG). Therefore, it is expected that the polymer micelle can avoid the foreign substance recognition mechanism in the body and renal excretion.

In consideration of the fact that the above-described plasmid DNA and antisense DNA are analogs of siRNA, the present inventors tried to form a siRNA-encapsulated polymer micelle using PEG-PLys as a strategy to improve disposition of siRNA. However, the product actually obtained had low structural stability and did not have a sufficient core-shell-type micelle structure of interest, and its ability to deliver siRNA into a culture cell was extremely low. Therefore, it was extremely difficult to utilize PEG-PLys as a carrier of siRNA.

DISCLOSURE OF THE INVENTION

One problem to be solved by the present invention is to provide a siRNA-encapsulated polymer micelle complex (a polyion complex), which has high monodispersibility and structural stability and is excellent in the ability of delivering siRNA into a cell. Another problem to be solved by the present invention is to provide a nucleic acid delivery device, a nucleic acid delivery kit, a pharmaceutical composition and a gene therapy agent, each of which comprises the complex.

The present inventors diligently made researches in order to solve the above-described problems, and thought that monodispersibility and structural stability of a polyion complex are low because siRNA is a molecule whose base length is extremely shorter compared to that of plasmid DNA, etc. In order to enable elimination of the causative factor, the present inventors made examination regarding various types of polyethylene glycol-polycation block copolymers, and found that the aforementioned problems can be solved by using a copolymer in which a highly basic functional group and a thiol group are introduced into the terminus of a sided chain of the polycation portion. Thus, the present invention was achieved.

Specifically, the present invention is as follows:
(1) A polyion complex, which comprises: a block copolymer constituted by a polyethylene glycol portion and a polycation portion having a side chain whose terminus is a thiol group; and siRNA.

Examples of the polycation portion in the polyion complex of the present invention include a polypeptide having a cationic group at a side chain thereof. Examples of the block copolymer include those represented by the following general formula (1):

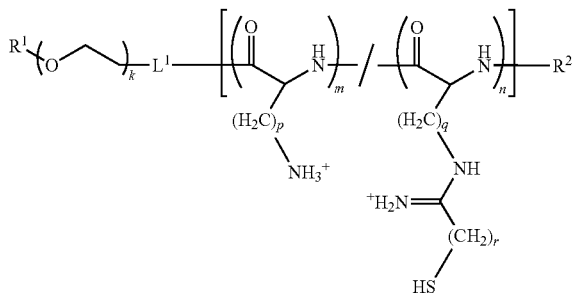

(1)

[wherein each of $R^1$ and $R^2$ independently represents a hydrogen atom or a substitutable linear or branched alkyl group containing 1 to 12 carbon atoms;
$L^1$ represents NH, a group represented by the following general formula (2):

$$-(CH_2)_{p1}-NH- \quad (2)$$

(wherein p1 represents an integer between 1 and 5), or a group represented by the following general formula (3):

$$-L^{2a}-(CH_2)_{q1}-L^{3a}- \quad (3)$$

(wherein $L^{2a}$ represents OCO, OCONH, NHCO, NHCOO, NHCONH, CONH or COO, $L^{3a}$ represents NH, and q1 represents an integer between 1 and 5);
k represents an integer between 100 and 500; m represents an integer between 0 and 499; n represents an integer between 1 and 500; and m+n=10 to 500;
p represents an integer between 1 and 10; q represents an integer between 1 and 10; and
r represents an integer between 1 and 10, and wherein the symbol "/" indicates that the sequence order of respective monomer units described at the left and right sides thereof (the number of units: m+n) is arbitrarily determined].

Examples of the polyion complex of the present invention include: those in which the polycation portion and siRNA bind to each other by electrostatic interaction; those in which the polycation portion and siRNA form a core portion, and the polyethylene glycol portion forms a shell portion around the core portion; and those in which an intramolecular and/or intermolecular disulfide bond is formed in the block copolymer.

(2) A device for delivering a nucleic acid into a cell, which comprises the polyion complex according to (1) above.
(3) A kit for delivering a nucleic acid into a cell, which comprises a block copolymer constituted by a polyethylene glycol portion and a polycation portion having a side chain whose terminus is a thiol group.

Examples of the kit of the present invention include those comprising the polyion complex according to (1) above.
(4) A pharmaceutical composition for treating cancer, which comprises the polyion complex according to (1) above.
(5) A gene therapy agent for cancer, which comprises the pharmaceutical composition according to (4) above as an active ingredient.
(6) A method for treating cancer, which comprises administering the pharmaceutical composition according to (4) above or the therapy agent according to (5) above to a patient.
(7) The polyion complex according to (1) above, which is for therapy for cancer (preferably for gene therapy for cancer).

(8) Use of the polyion complex according to (1) above, which is for producing a medicinal product for treating cancer.

EXPLANATIONS OF LETTERS OR NUMERALS 1 block copolymer
2 polyethylene glycol (PEG) portion
3 polycation portion
4 siRNA
5 polyion complex (PIC)

BEST MODE FOR CARRYING OUT THE INVENTION

Hereinafter, the present invention will be described in detail. The scope of the present invention is not limited to the description. In addition to the following examples, the present invention can be suitably changed and then practiced within a range in which the effects of the present invention are not reduced.
Note that the entire specification of Japanese Patent Application No. 2006-315753, to which priority is claimed by the present application, is incorporated herein. In addition, all the publications such as prior art documents, laid-open publications, patents and other patent documents cited herein are incorporated herein by reference.
1. Outline of the Present Invention
Regarding formation of a siRNA-encapsulated polymer micelle complex (polyion complex), the present inventors thought that a polymeric block copolymer, which functions as a carrier of siRNA (polyethylene glycol-polycation block copolymer), must be modified in order to improve monodispersibility and structural stability of the polyion complex, and made examination from various angles.
The present inventors prepared a siRNA-encapsulated polyion complex using a block copolymer in which a thiol group (—SH group) was introduced into the terminus of a side chain of a polycation portion. Specifically, a siRNA-encapsulated polyion complex was prepared using a block copolymer in which a 1-imino-4-mercaptobutyl group including a —SH group was introduced into a primary amine of a polymeric block copolymer consisting of polyethylene glycol (PEG) and polylysine (PLys) (hereinafter referred to as PEG-PLys (SH+)).

Figure 1:
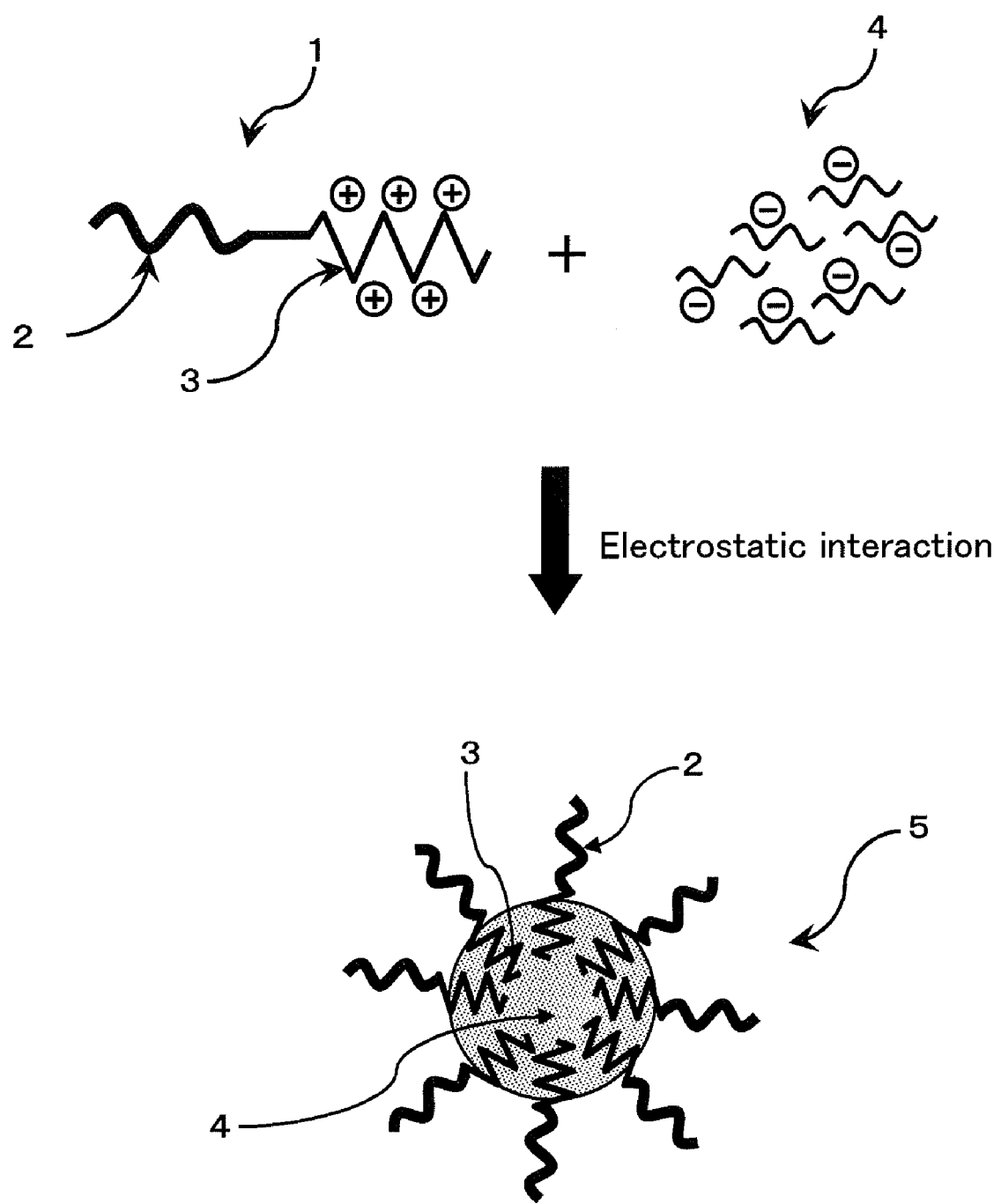
FIG. 1 is a schematic diagram showing the structure of the polyion complex of the present invention.

As a result, the present inventors succeeded in the formation of micelle-like polyion complex having a core-shell-type structure, which is a nanometer-scale structure into which a polyanion, siRNA is stably encapsulated, and which is excellent in monodispersibility and structural stability (see FIG. 1).

Further, in the obtained siRNA-encapsulated polyion complex, a cross-linked structure may be formed by a disulfide (—S—S—) bond when thiol groups (—SH groups) at the terminuses of the side chains of the polycation portion are reacted with each other. By this bond, associating property between the aforementioned block copolymers constituting the polyion complex is enhanced. Therefore, even in the case of a molecule having a short base length such as siRNA, a stable state of encapsulation can be retained, and as a result, the micelle structure can be effectively stabilized. Moreover, since the stability of the cross-linked structure made by disulfide bond varies depending on change in environments inside/outside cells, by utilizing this, a high ability to deliver siRNA into a cell can be achieved. That is, disulfide bond is easily cleaved in the reductive environment, and there is a difference in oxidation-reduction environment between the extracellular area and the intracellular area depending on the difference in glutathione concentration. Specifically, the extracellular area is in the non-reductive environment (about 10 μM), and the intracellular area is in the reductive environment (about 10 mM). Therefore, after the polyion complex of the present invention is taken into a target cell, stabilization provided by the cross-linked structure is broken, and accordingly, the encapsulated siRNA can be smoothly and efficiently released into a target cell. As a result, gene expression suppression efficiency (knockdown efficiency) provided by RNAi and the like can be dramatically improved.

Thus, the polyion complex of the present invention can hold siRNA, which is an easily-degradable and unstable chemical species under physiological circumstances, in an extremely stable state until it is introduced into a target cell. Moreover, the polyion complex of the present invention is highly useful as an intelligent vector which can efficiently release siRNA (introduce siRNA into a cell) responding to change in environment from the extracellular area through the intracellular area.

The block copolymer to be used in the polyion complex of the present invention is disclosed in a document written by the present inventors which was already published (Miyata, K. et al., J. Am. Chem. Soc., vol. 126, pp. 2355-2361, 2004) (e.g., polymer designated as "PEG-PLL-IM" in Scheme 1 in page 2356). However, the purpose of the document is to report a block copolymer which is useful as a carrier for pDNA, and the document does not disclose that the block copolymer is used as a carrier for siRNA. That is, the document discloses the block copolymer to be used in the present invention as a comparative polymer which does not show utility as a carrier for pDNA. Further, though both pDNA and siRNA belong to the group of nucleic acids, as described above, it was difficult to use the existing block copolymer, which is useful as a carrier for pDNA, etc., as a useful carrier for siRNA. Under such circumstances, the present inventors found that siRNA, which had significant difficulty in stable encapsulation, can be encapsulated in a micelle-like polyion complex at a sufficient practical level by using the block copolymer, which is disclosed in the document as the comparative polymer, as a carrier for siRNA. Moreover, the present inventors found that this siRNA-encapsulated polyion complex exerts remarkable effects as a device for delivering siRNA, which are more than expected by those skilled in the art (for example, the polyion complex realizes a extremely high efficiency of introducing siRNA into a target cell).

2. Polyion Complex

The polyion complex (PIC) of the present invention is a micelle-like siRNA-encapsulated polymer complex, which comprises: a specific block copolymer including a polycation portion having a side chain in which a thiol group is introduced into the terminus thereof; and siRNA.

(1) Block Copolymer

The block copolymer which constitutes the PIC of the present invention is a block copolymer which comprises the PEG portion and the polycation portion as its constituents, and it is characterized in that the polycation portion has a side chain in which a thiol group (—SH group) is introduced into the terminus thereof.

In the polycation portion, a —SH group, which is to be introduced into the terminus of the side chain, may be introduced into at least a part of side chains which the polycation portion has. Regarding the introduction ratio, for example, among all the side chains which the polycation has, preferably 0.2 to 100%, more preferably 5 to 70%, and even more preferably 30 to 65% of the side chains have —SH group at the terminus thereof.

The structures (e.g., polymerization degree) of the PEG portion and the polycation portion are not limited except for the above-described matter of —SH group at the terminus, and any structure can be selected. The polycation portion is particularly preferably a polypeptide having a cationic group at its side chain. The cationic group as used herein means not only a group which is already a cation with hydrogen ion coordinated, but also a group which will become a cation when hydrogen ion is coordinated. Examples of the cationic group include all the publicly-known cationic groups. Examples of polypeptides having a cationic group at the terminus thereof include: products in which publicly-known amino acids having a basic side chain (lysine, arginine, histidine, etc.) bind to each other via peptide bond; and products, in which various amino acids bind to each other via peptide bond, and after binding, the side chain thereof is subjected to substitution to have a cationic group.

Preferred examples of the block copolymer to be used in the present invention include a block copolymer represented by the following general formula (1):

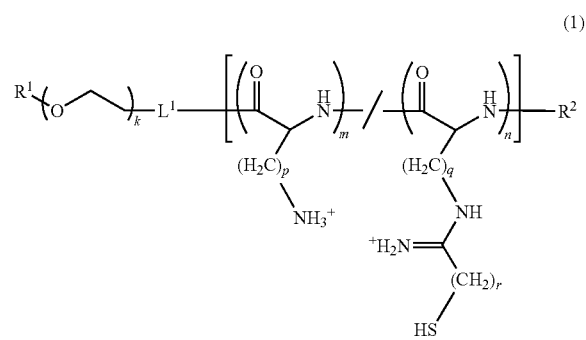

(1)

In this regard, in the structural formula in general formula (1), a block portion with the number of repeat unit (polymerization degree) of k is a PEG portion, and a block portion consisting of a portion with the number of repeat unit of m and a portion with the number of repeat unit of n (a portion put in brackets "[ ]" in general formula (1)) is a polycation portion. Further, the symbol "/" in the polycation portion means that the sequence order of respective monomer units described at the left and right sides thereof is arbitrarily determined. For example, when a block portion constituted by monomer units A and B is expressed as $[-(A)_a-/-(B)_b-]$, it means that respective monomer units (the total number of units: a+b) consisting of monomer unit As (the number thereof: a) and monomer unit Bs (the number thereof: b) may be linked to each other in any order. However, all the monomer unit As and Bs must be liked to each other in a linear manner.

In general formula (1), $R^1$ and $R^2$ independently represents a hydrogen atom or a substitutable linear or branched alkyl group containing 1 to 12 carbon atoms.

Examples of linear or branched alkyl groups containing 1 to 12 carbon atoms include methyl group, ethyl group, n-propyl group, isopropyl group, n-butyl group, sec-butyl group, tert-butyl group, n-pentyl group, n-hexyl group, decyl group, and undecyl group.

Examples of substituents for alkyl groups include acetalized formyl group, cyano group, formyl group, carboxyl group, amino group, alkoxycarbonyl group containing 1 to 6 carbon atoms, acylamide group containing 2 to 7 carbon atoms, siloxy group, silylamino group, and trialkylsiloxy group (each alkylsiloxy group independently contains 1 to 6 carbon atoms).

When the substituent is an acetalized formyl group, by hydrolyzing it under acidic and mild conditions, it can be transformed into another substituent, formyl group (aldehyde group; —CHO). When the substituent (particularly substituent in $R^1$) is a formyl group, carboxyl group or amino group, for example, an antibody, a fragment thereof, a protein having another functionality or target-directed property or the like can be linked via the above-described group.

In general formula (1), $L^1$ is a linker portion between the PEG portion and the polycation portion, and represents NH, a group represented by the following general formula (2):

$$—(CH_2)_{p1}—NH— \quad (2)$$

(wherein p1 represents an integer between 1 and 5 (preferably between 2 and 3)), or a group represented by the following general formula (3):

$$-L^{2a}-(CH_2)_{q1}-L^{3a}- \quad (3)$$

(wherein $L^{2a}$ represents OCO, OCONH, NHCO, NHCOO, NHCONH, CONH or COO, $L^{3a}$ represents NH, and q1 represents an integer between 1 and 5 (preferably between 2 and 3)).

In general formula (1), k represents the number of repeat units (polymerization degree) in the PEG portion. Specifically, k represents an integer between 100 and 500 (preferably between 200 and 300).

With respect to the polymerization degree of each of the monomer units constituting the polycation portion, m represents an integer between 0 and 499 (preferably between 1 and 100, more preferably between 20 and 100, even more preferably between 30 and 100, and particularly preferably between 30 and 70), and n represents an integer between 1 and 500 (preferably between 1 and 100, more preferably between 5 and 100, even more preferably between 5 and 50, and particularly preferably between 10 and 50). In this regard, m+n equals 10 to 500 (preferably 10 to 200, more preferably 20 to 150, even more preferably 30 to 120, still more preferably 30 to 100, still even more preferably 40 to 100 and particularly preferably 40 to 70).

With respect to the number of repeat units, methylene groups ($—CH_2—$) in side chains in the polycation portion, p represents an integer between 1 and 10 (preferably between 3 and 4), q represents an integer between 1 and 10 (preferably between 3 and 4), and r represents an integer between 1 and 10 (preferably between 2 and 4).

According to the above-described matters, it can be said that the polymer represented by general formula (1) has the following two block portions as essential constituents.

a block portion consisting of a polyethylene glycol (PEG) chain which is hydrophilic and has excellent biocompatibility (a block portion with the polymerization degree of k: PEG portion)

a block portion having a side chain which electrostatically binds to siRNA and a side chain which can form a cross-linked structure provided by disulfide bond with another side chain (a block portion having a cationic group and a terminal thiol group at the side chain thereof with the polymerization degree of m+n: polycation portion)

The molecular weight (Mw) of the block copolymer represented by general formula (1) is not limited, but is preferably 10,000 to 150,000, and more preferably 10,000 to 40,000. Regarding respective block portions, the molecular weight (Mw) of the PEG portion is not limited, but is preferably 4,400 to 22,000, more preferably 8,000 to 15,000, even more preferably 10,000 to 13,000, and particularly preferably 10,000 to 12,000. The molecular weight (Mw) of the polycation portion is not limited, but is preferably 2,500 to 125,000, and more preferably 2,500 to 25,000.

The method for producing the polymer represented by general formula (1) is not limited. Roughly summarized, one example of the method includes: (a) a segment including $R^1$ and the block portion of PEG chain (PEG segment) is synthesized in advance; (b1) predetermined monomers are sequentially polymerized at one end of the PEG segment (the end opposite to $R^1$), and after that, according to need, a side chain is subjected to substitution or conversion to include a cationic group; or (b2) the above-described PEG segment and the block portion having a side chain including a cationic group are linked to each other by synthesis in advance; and (c) after that, a —SH group-containing compound is reacted with the side chain including a cationic group, thereby introducing the —SH group into the terminus of the side chain. In the production method, reaction methods and conditions can be suitably selected or set in consideration of the ordinary method. As a specific example of the production method, the synthesis scheme in the Examples described below can be referred to.

The above-described PEG segment can be prepared using, for example, the method for producing a PEG segment portion of a block copolymer described in International Publication WO 96/32434 pamphlet, International Publication WO 96/33233 pamphlet, or International Publication WO 97/06202 pamphlet. In the PEG segment, the terminus opposite to —$R^1$ group is a portion "-$L^1$" in general formula (1), and is preferably —$NH_2$, a group represented by the following general formula (4):

$$—(CH_2)_{p2}—NH_2 \quad (4)$$

(wherein p2 represents an integer between 1 and 5 (preferably between 2 and 3)), or a group represented by the following general formula (5):

$$-L^{2b}-(CH_2)_{q2}-L^{3b} \quad (5)$$

(wherein $L^{2b}$ represents OCO, OCONH, NHCO, NHCOO, NHCONH, CONH or COO, $L^{3b}$ represents $NH_2$, and q2 represents an integer between 1 and 5 (preferably between 2 and 3)).

(2) Encapsulated Nucleic Acid

In one embodiment, a nucleic acid encapsulated as a constituent of the core portion in the PIC of the present invention is siRNA (small interfering RNA). Any siRNA may be used as long as it can suppress expression of a gene of interest utilizing RNA interference (RNAi). Preferred examples of the gene of interest include cancer (tumor) gene, antiapoptosis gene, cell cycle-related gene, proliferative signal gene, etc. Usually, siRNA may have any base length as long as it is less than 30 bases (preferably 19 to 21 bases), and there is no limitation regarding this.

However, in the present invention, a nucleic acid to be encapsulated is not limited to siRNA, and according to need, other nucleic acids such as plasmid DNA and antisense oligo DNA, decoy nucleic acid (double-stranded DNA), various RNAs, and chemically-modified nucleic acid and analogs of non-naturally occurring type nucleic acid (e.g., PNA (peptide nucleic acid)) can also be encapsulated.

Since a nucleic acid molecule such as siRNA becomes a polyanion, it can be bound to (associated with) a side chain of the polycation portion of the aforementioned block copolymer by electrostatic interaction.

In the present invention, according to need, various substances which provide functional expression in a cell such as physiologically active protein and various peptides can be included in the core portion together with the above-described siRNA or the like.

In another embodiment of the PIC of the present invention, as a constituent of the core portion, a high-molecular weight or low-molecular weight "anionic substance" can be further used. Examples thereof include high-molecular weight substances such as virus particles, peptide hormone, protein and enzyme, and low-molecular weight substances having a charged functional group within a molecule (water-soluble compounds). Examples of the anionic substances also include a product which can alter the charged state of the entire molecule having a plurality of functional groups with different charged states (anionic groups and cationic groups) into an anionic state by changing pH. These anionic substances can be used solely or in combination, and there is no limitation regarding this.

(3) Polyion Complex (PIC)

It can be said that the PIC of the present invention is a core-shell-type micelle-like complex in which siRNA and a portion in the block copolymer (the polycation portion) interact with each other to form a core portion as an ion complex, and other portions in the block copolymer (portions including the PEG portion) form a shell portion around the core portion (see FIG. 1).

The PIC of the present invention can be easily prepared, for example, by mixing siRNA with the block copolymer in any buffer (e.g., Tris buffer). However, preparation thereof is preferably carried out under sufficient reducing conditions so that only the block copolymer would not perform aggregation or the like via disulfide bond prior to electrostatic bond between the block copolymer and siRNA. The reducing conditions can be adjusted, for example, by addition of DTT (Dithiothreitol) or the like.

In addition, in the PIC of the present invention, after the electrostatic binding between the block copolymer and siRNA (after the formation of the micelle structure), oxidizing conditions are provided by addition of DMSO or the like to react —SH groups in the block copolymer with each other, thereby forming intramolecular and/or intermolecular disulfide-cross-linked structure in the block copolymer. This cross-linked structure makes it possible to further stabilize the encapsulated state of siRNA and the micelle structure.

The mixing ratio between the block copolymer and siRNA is not limited. However, for example, the ratio between the total number of cationic groups (e.g., amino groups) in the block copolymer (N) and the total number of phosphate groups in siRNA (P) (N/P ratio) is preferably 0.5 to 100, more preferably 0.5 to 10, even more preferably 1 to 10, still more preferably 1 to 4, and particularly preferably 1 to 2. Even when the block copolymer is a copolymer of general formula (1), as in the case described above, the N/P ratio is preferably 0.5 to 10, more preferably 0.5 to 4, and even more preferably 1 to 2 ("N" in this case is the total number of primary amines and secondary amines contained in side chains of the polycation portion). When the N/P ratio is within the above-described range, it is preferred, for example, on the point that there is no free polymer and high expression efficiency can be obtained in vivo. The above-described cationic group (N) means a group which can form ion bond by electrostatic interaction with a phosphate group in a nucleic acid encapsulated.

The size of the PIC of the present invention is not limited. However, for example, the particle diameter according to the dynamic light scattering measurement method (DLS) is preferably 30 to 150 nm, and more preferably 50 to 100 nm.

3. Nucleic Acid Delivery Device

The present invention provides a nucleic acid delivery device including the above-described polyion complex (PIC). The delivery device of the present invention makes it possible to easily stabilize siRNA, which was difficult to be delivered with its stable state retained into a target cell. Therefore, even if the use amount of siRNA is small, efficient effects of RNAi, etc. can be exerted. In addition, the delivery device can be used as a means for efficiently introducing desired siRNA encapsulated in the core portion of the PIC into a target cell by utilizing change in oxidation-reduction environment from the extracellular area through the intracellular area.

For example, a solution containing the PIC in which desired siRNA is encapsulated is administered to a test animal to be taken into a target cell in its body. After that, the PIC taken into the cell migrates from endosome to cytoplasm. When disulfide bond has been formed between block copolymers, the bond is cleaved responding to the reductive environment in cytoplasm. As a result, replacement of polyanion present in the cell with siRNA encapsulated in the PIC is promoted, and by disassociation of the PIC, the desired siRNA can be released in cytoplasm.

The delivery device of the present invention may be applied to various animals such as human, mouse, rat, rabbit, swine, dog and cat, and there is no limitation regarding this. Usually, as a method for administering to a test animal, a parenteral method such as drip infusion is employed. Conditions such as dosage amount, number of doses and dosing period can be suitably set depending on the type and condition of the test animal.

The delivery device of the present invention can be used in a treatment in which desired siRNA is introduced into cells which cause various diseases (gene therapy). Therefore, the present invention can also provide: a pharmaceutical composition including the aforementioned PIC for treating various diseases; a gene therapy agent for various diseases, which includes the pharmaceutical composition as an active ingredient; and a method for treating various diseases using the aforementioned PIC (in particular, gene therapy method). A method and conditions of administration may be employed as in the case described above. Examples of various diseases include cancer (e.g., lung cancer, pancreatic cancer, brain tumor, liver cancer, breast cancer, large intestine cancer, neuroblastoma and bladder cancer), cardiovascular disease, locomotor apparatus disease, and central nervous system disease.

Excipients, fillers, bulking agents, binders, wetting agents, disintegrants, lubricants, surfactants, dispersing agents, buffering agents, preservatives, solubilizing agents, antiseptic agents, flavoring agents, soothing agents, stabilizing agents, tonicity agents and the like, which are generally used in production of agents, may be suitably selected and used, thereby preparing the above-described pharmaceutical composition according to the ordinary method. Further, as the form of the pharmaceutical composition, intravenous injection (including drip infusion) is usually employed, and for example, the composition is provided in the form of unit dose ampule or multiple-dose container.

4. Nucleic Acid Delivery Kit

The nucleic acid delivery kit of the present invention is characterized in that it comprises the aforementioned specific block copolymer or the polyion complex of the present invention. The kit may be preferably used, for example, in gene therapy utilizing RNAi, in which siRNA is introduced into various target cells such as cancer cells.

In the kit of the present invention, the state of preservation of the block copolymer is not limited. In consideration of its stability (preservative quality), easiness of use, etc., a solution state, powder state or the like can be selected.

In addition to the aforementioned specific block copolymer, the kit of the present invention may comprise other constituents. Examples of such other constituents include siRNA to be introduced into a cell, various buffers for dissolution, dilution or the like, buffer for dissolution, various proteins, and an instruction for use (manual).

The kit of the present invention is used to prepare a polyion complex (PIC) having desired siRNA to be introduced into a target cell as the core portion, and the prepared PIC can be effectively used as a device for delivering siRNA into a target cell.

EXAMPLES

Hereinafter, the present invention will be specifically described by way of illustrative examples, but the present invention is not limited thereto.

Example 1

Materials

Names, abbreviated names, providers, etc. of compounds, apparatuses, etc. used in the examples will be described below:
ε-benzyloxycarbonyl-L-lysine (Lys (Z)) (Sigma-Aldrich)
n-hexane tetrahydrofuran (THF) (Wako Pure Chemical Industries, Ltd.)
Triphosgene (Tokyo Chemical Industry Co., Ltd.)
α-methoxy-ω-amino-polyethylene glycol (molecular weight: 12,000) (Nippon Oil & Fats)
Chloroform (Wako Pure Chemical Industries, Ltd.)
Diethyl ether (Showa Ether Corporation)
Benzene (Wako Pure Chemical Industries, Ltd.)
N,N-dimethylformamide (DMF) (Wako Pure Chemical Industries, Ltd.)
Trifluoroacetic acid (Wako Pure Chemical Industries, Ltd.)
30% HBr/$CH_3COOH$ (Tokyo Chemical Industry Co., Ltd.)
Lithium chloride (Wako Pure Chemical Industries, Ltd.)
N-methylpyrrolididone (NMP) (Sigma-Aldrich)
Diisopropylethylamine (DMA) (Wako Pure Chemical Industries, Ltd.)
2-iminothiolane (Wako Pure Chemical Industries, Ltd.)
0.01 mol/L hydrochloric acid (Wako Pure Chemical Industries, Ltd.)
IR-Report 100 (JASCO Corporation)
NMR EX400 spectrometer (JEOL Ltd.)
HLC-8820 GPC (TOSOH Corporation)
2-[4-(2-hydroxyethyl)-1-piperazinyl]ethanesulfonic acid (HEPES) (DOJINDO)
Dithiothreitol (DTT) (Wako Pure Chemical Industries, Ltd.)
Dimethyl sulfoxide (DMSO) (Wako Pure Chemical Industries, Ltd.)
Zetasizer (Malvern)
SYBR Green II (Molecular Probes)
Dulbecco's modified Eagle medium (DMEM) (Sigma-Aldrich)
siRNA (21 bp (double-stranded): SEQ ID NO: 1, 2) (Dharmacon)
Sense strand: 5'-CUUACGCUGAGUACUUCGAdTdT-3' (SEQ ID NO: 1)
Antisense strand: 5'-UCGAAGUACUCAGCGUAAGdTdT-3' (SEQ ID NO: 2)
Mini dialysis kit (molecular weight cut off (MWCO)=1,000) (Amersham)
Dual-Luciferase (registered trademark) Reporter Assay System (Promega)
Mithras LB-940 (Berthold)

<Methods>

1. Synthesis of Lys(Z)-N-carboxy anhydride (Lys(Z)-NCA)

25 g of Lys(Z) was dried under reduced pressure overnight, and 200 mL of THF was added thereto under argon atmosphere to suspend Lys(Z). Triphosgene/THF solution was added to the mixture to provide phosgene in an amount of 1.3 times by equivalent that of Lys(Z), and reaction was performed at 50° C. until the solution became transparent and colorless. After the reaction was complete, the solution was added dropwise to 750 mL of n-hexane (poor solvent) under Ar atmosphere to cause reprecipitation, and the mixture was allowed to stand at −20° C. After that, supernatant was removed from the mixture, and then the obtained product was dried under reduced pressure. Lys(Z)-NCA was dissolved in THF again. Hexane was added thereto until a small amount of crystal was precipitated, and it was allowed to stand at −20° C. overnight. The crystal was separated from supernatant. Lys (Z)-NCA was recrystallized again, and thereafter it was dried under reduced pressure and then the crystal of Lys(Z)-NCA was collected. The supernatant was repeatedly subjected to recrystallization operation in the same way, and thereafter crystal of Lys(Z)-NCA was obtained.

2. Purification of Polyethylene Glycol (PEG)

To α-methoxy-ω-amino-polyethylene glycol having a primary amino group at one end thereof (molecular weight: 12,000), chloroform in an amount of 3 times greater was added for dissolution. Next, the obtained mixture was added dropwise to diethyl ether (in an amount of 20 times greater than that of chloroform; poor solvent) at 0° C. to cause reprecipitation, and precipitate was collected by means of suction filtration. After that, to the collected precipitate, benzene was added for dissolution, and the obtained mixture was subjected to freeze dry to collect PEG 3. Synthesis of PEG-PLys(Z)

DMF was added to PEG purified under argon atmosphere and the synthesized Lys(Z)-NCA for dissolution, respectively, to obtain 100 mg/mL of solutions thereof. The PEG solution was added to the Lys(Z)-NCA solution, and reaction was performed at 40° C. The disappearance of absorption peaks at 910 cm$^{-1}$ (C—O stretch), 1,780 cm$^{-1}$ (C=O stretch) and 1,850 cm$^{-1}$ (C'O stretch) derived from acid anhydride ring of N-carboxy anhydride (NCA) was confirmed by IR measurement, and the reaction was completed. After the completion of reaction, DMF was evaporated at 40° C. by an evaporator. Chloroform was added to the residue obtained after evaporation for dissolution, and reprecipitation was performed using diethyl ether at 0° C. to collect precipitate by means of suction filtration. After that, the collected precipitate was subjected to freeze dry to collect PEG-PLys(Z). The polymer structure of the obtained PEG-PLys(Z) was confirmed by measurement of $^1$H-NMR and gel permeation chromatography (GPC).

4. Deprotection of PEG-PLys(Z)

Trifluoroacetic acid was added to the synthesized PEG-PLys(Z) for dissolution. After that, 30% HBr/CH$_3$COOH was added to the mixture, and reaction was performed for 4 hours. After the completion of the reaction, reprecipitation and washing were performed twice, respectively, using diethyl ether at 0° C. After diethyl ether was removed, pure water was added to the obtained polymer for dissolution, and the solution was dialyzed against pure water in an amount of 200 times greater (using a dialysis membrane (MWCO=1,000)) to remove salt. After the completion of dialysis, the obtained product was subjected to freeze dry to collect polymer. $^1$H-NMR measurement was performed, and based on the disappearance of peak derived from a Z group as a protecting group, completion of deprotection was confirmed.

5. Synthesis of PEG-PLys(SH+)

100 mL of NMP was added to 5 g of lithium chloride under argon atmosphere, thereby dissolving lithium chloride. This NMP was added to the deprotected PEG-PLys for dissolution, and PEG-PLys was deprotonated by addition of DIEA. After 2-iminothiolane was added to the mixture, it was protected from light, and reaction was performed for 48 hours. Using diethyl ether from which oxygen was removed by argon bubbling, reprecipitation and washing was performed twice, respectively. After diethyl ether was removed, 0.01 mol/L of hydrochloric acid was added to the obtained polymer for dissolution, and the solution was dialyzed against pure water in an amount of 100 times greater (using a dialysis membrane (MWCO=2,000)) to remove salt. After the completion of dialysis, the obtained product was subjected to freeze dry to collect polymer. $^1$H-NMR measurement was performed, and the thiol group introduction rate was calculated based on peak derived from newly-occurring introduced groups.

6. Measurement of Scattered Light Intensity of PEG-PLys(SH+)/siRNA Mixed Solution siRNA (SEQ ID NO: 1, 2) was dissolved in 10 mM HEPES-NaOH (pH 7.4) to obtain the concentration of 15 µM. The siRNA used can suppress gene expression of luciferase (Pp-Luc) by RNAi. In the same way, PEG-PLys(SH+) was dissolved in 10 mM HEPES-NaOH (pH 7.4). Subsequently, the siRNA solution was mixed with ½ volume of the PEG-PLys(SH+) solution at a concentration which realizes the target N/P ratio (+/− charge ratio). The obtained mixture was allowed to stand at 25° C. for 24 hours, and after that, scattered light intensity was measured using Zetasizer.

7. Polyacrylamide Gel Electrophoresis of PEG-PLys(SH+)/siRNA Mixture

PEG-PLys(SH+)/siRNA mixtures formed to have different N/P ratios were subjected to 20% NATIVE-PAGE (non-degenerated polyacrylamide gel electrophoresis), and free siRNA was detected by means of SYBR Green II stain and a UV transilluminator.

8. Preparation of PEG-PLys(SH+)/siRNA Micelle

Each of PEG-PLys(SH+) and siRNA was dissolved in 10 mM HEPES-NaOH (pH 7.4), thereby providing stock solutions thereof. Subsequently, a large excess of DTT was added to PEG-PLys(SH+) to reduce thiol groups, and this was mixed with siRNA at a mixing ratio which provides a near-neutral charge (N/P=1 to 2). After the mixture was allowed to stand at 25° C. for 24 hours, dialysis was performed using Mini dialysis kit to remove DTT, and in addition, 0.5% DMSO as an oxidant was added to the external solution, thereby carrying out treatment to form disulfide cross-linkings. The formation of disulfide cross-linkings was confirmed by the Ellman method, which is a quantitation method for free thiol groups.

9. Measurement of Particle Size Distribution of PEG-PLys(SH+)/siRNA Micelle 150 mM NaCl was added to PEG-PLys(SH+)/siRNA micelle, and the mixture was subjected to the measurement of dynamic light scattering at 37° C. using Zetasizer.

10. Measurement of Zeta Potential of PEG-PLys(SH+)/siRNA Micelle 150 mM NaCl was added to PEG-PLys(SH+)/siRNA micelle, and the mixture was subjected to the measurement of zeta potential at 37° C. using Zetasizer.

11. Evaluation of Stability of PEG-PLys(SH+)/siRNA Micelle 0 to 600 mM NaCl was added to PEG-PLys(SH+)/siRNA micelle. The mixture was allowed to stand at 37° C. for 24 hours, and thereafter it was subjected to the measurement of scattered light intensity using Zetasizer.

12. Transfection of siRNA into Culture Cell

Huh7 cells (human hepatoma-derived cells) were cultured under the following conditions: 10% FBS DMEM; 5% CO$^2$; and 37° C. 20 hours after the seeding, pGL3-Control (firefly luciferase expression vector) and pRL-CMV (*Renilla luciferase* expression vector) were introduced by Lipofectamine-2000™. Subsequently, 4 hours after the introduction, the medium was replaced by another one, and the PEG-PLys(SH+)/siRNA micelle in which siRNA against firefly luciferase was encapsulated was added to the medium. 48 hours after the addition of the micelle, luciferase was quantified by means of Dual-Luciferase (registered trademark) Reporter Assay System and a plate reader (Mithras LB-940).

<Results and Discussion>

1. Synthesis of PEG-PLys(SH+)

Figure 2:
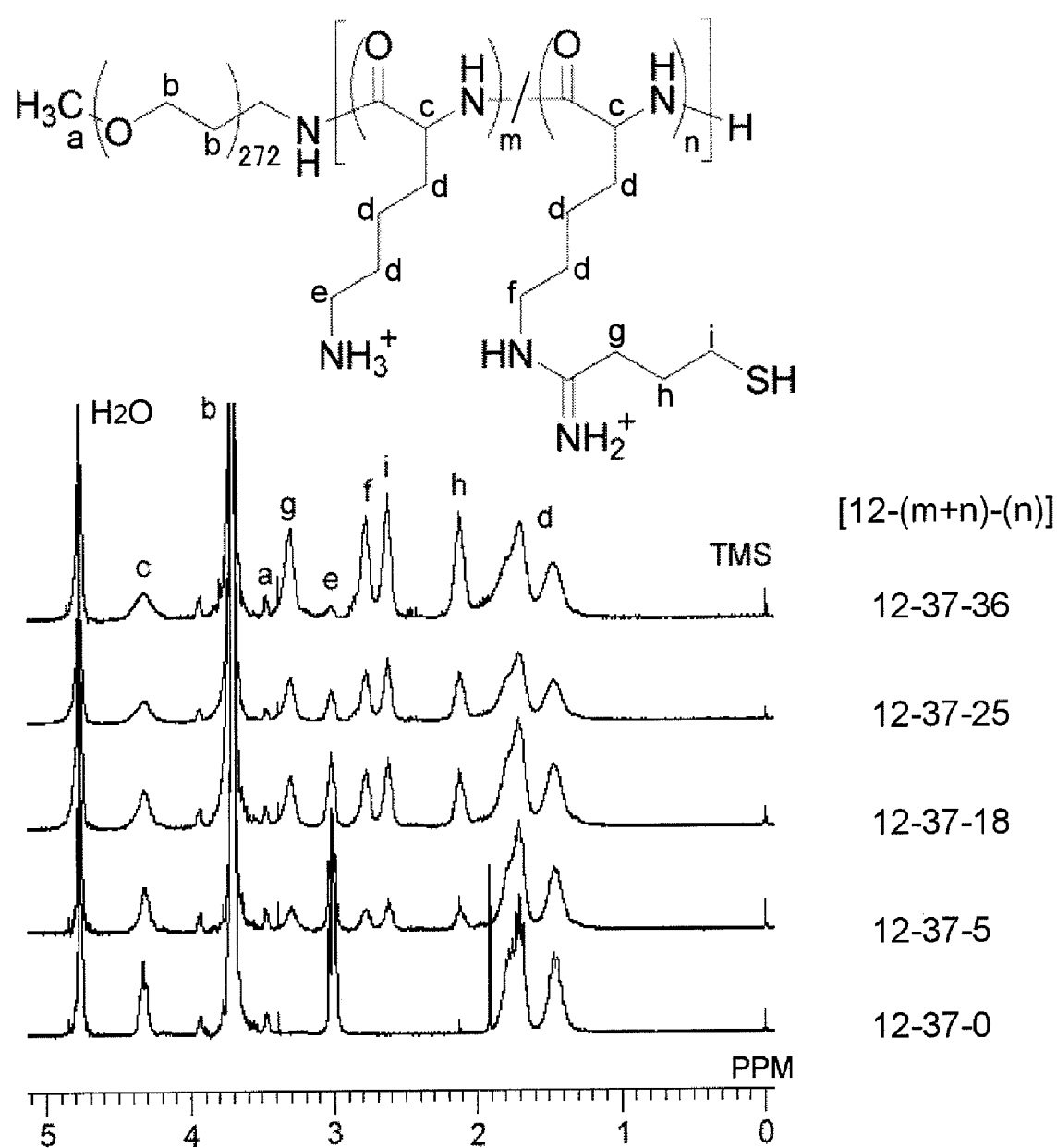
FIG. 2 shows the chemical structural formula of PEG-PLys (SH+) and $^1$H-NMR spectrum of PEG-PLys (SH+). In the structural formula, the symbol "/" means that the sequence order of respective monomer units described at the left and right sides thereof (the number of units: m+n) is arbitrarily determined.

PEG-PLys(SH+) was synthesized according to the synthesis scheme described below. The polymerization degree of lysine residue in PEG-PLys is 37. By changing the ratio of reaction between PEG-PLys and 2-iminothiolane, a plurality of PEG-PLys(SH+) products with different efficiencies of introduction of 1-imino-4-mercaptobutyl group were obtained. The composition of the monomer unit constituting the PLys(SH+) portion (i.e., the polycation portion) in PEG-PLys(SH+) was calculated based on the integration ratio of $^1$H-NMR spectrum shown in FIG. 2.

In the present specification and drawings, the composition of PEG-PLys(SH+) is generally represented by 12–(m+n)–(n). In this regard, "12" represents the presence of the PEG portion, and is an abbreviation of PEG having the molecular weight of 12,000 (PEG12,000). "m" represents the polymerization ratio of Lys residue (no introduction of —SH group) in the PLys(SH+) portion. "n" represents the polymerization ratio of Lys residue into which 1-imino-4-mercaptobutyl group (containing —SH group) is introduced in the PLys (SH+) portion. In the chemical structural formula in the synthesis scheme described below, the symbol "/" means that the sequence order of respective monomer units described at the left and right sides thereof (the number of units: m+n) is arbitrarily determined.

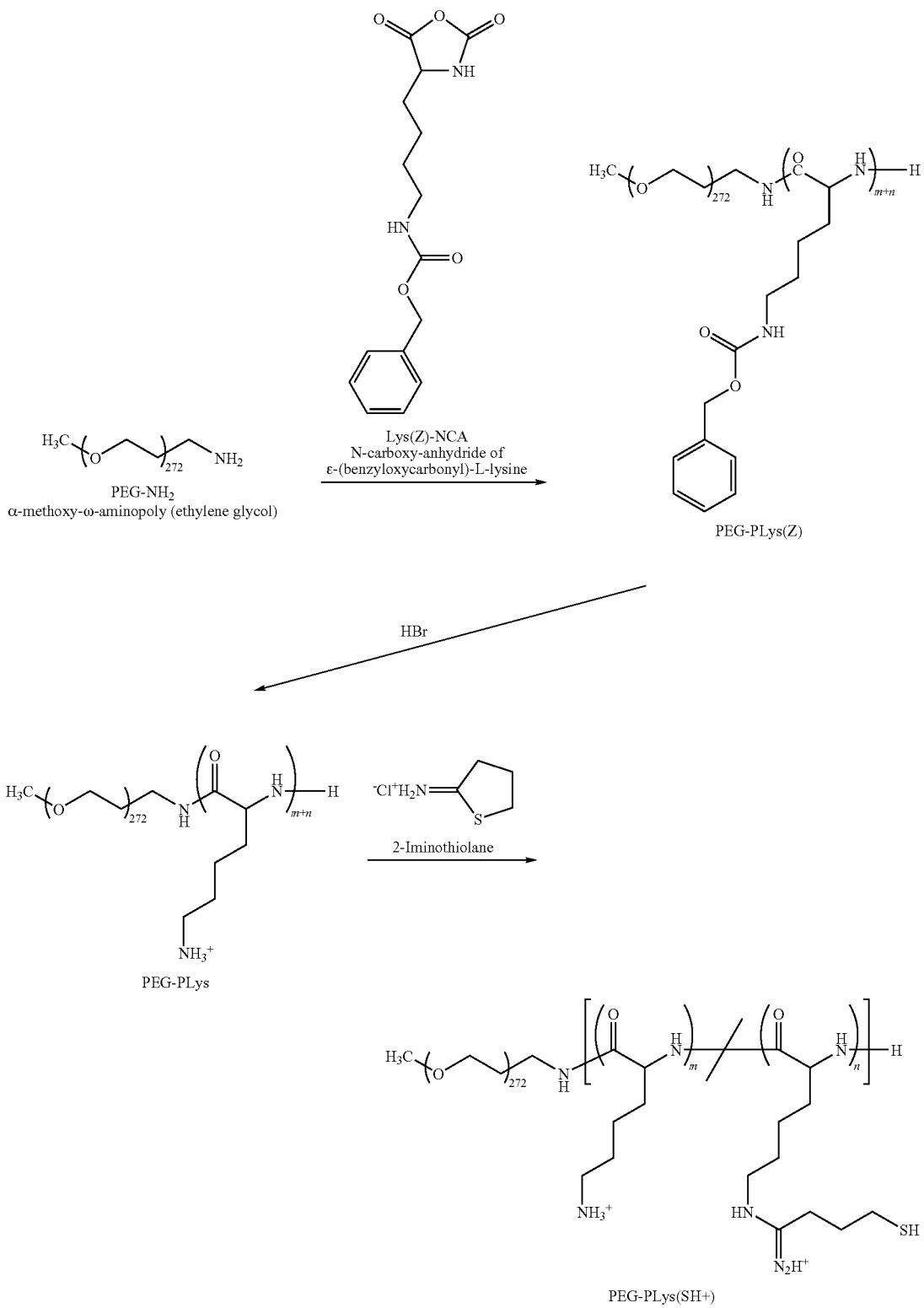

2. Examination of Mixing Ratio Between PEG-PLys(SH+) and siRNA

In order to examine conditions for the formation of polymer micelle between PEG-PLys(SH+) and siRNA, PEG-PLys(SH+)/siRNA solutions prepared by changing the mixing ratio between PEG-PLys(SH+) and siRNA were subjected to the measurement of scattered light intensity.

Figure 3:
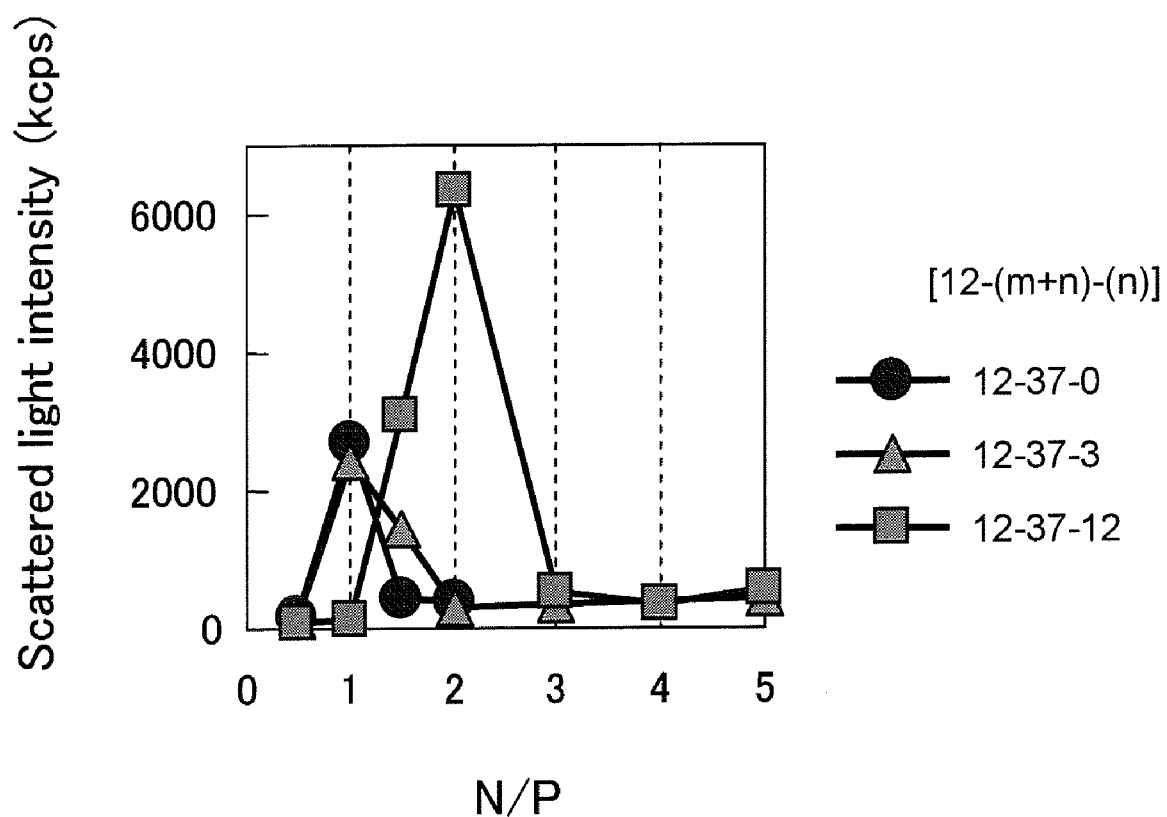
FIG. 3 is a graph showing the relationship between the mixing ratio between PEG-PLys (SH+) and siRNA (N/P) and the scattered light intensity with respect to PEG-PLys (SH+)/siRNA micelle.

As a result, at the N/P ratio of 1 to 2, which provides a near-neutral charge, strong scattered light, which indicates the presence of an assembly having a large molecular weight, was obtained (FIG. 3). It was thought that this assembly was a siRNA-encapsulated polymer micelle.

3. Polyacrylamide Gel Electrophoresis of PEG-PLys(SH+)/siRNA

Complexes formed by changing the mixing ratio between PEG-PLys(SH+) and siRNA were subjected to NATIVE-PAGE.

Figure 4:
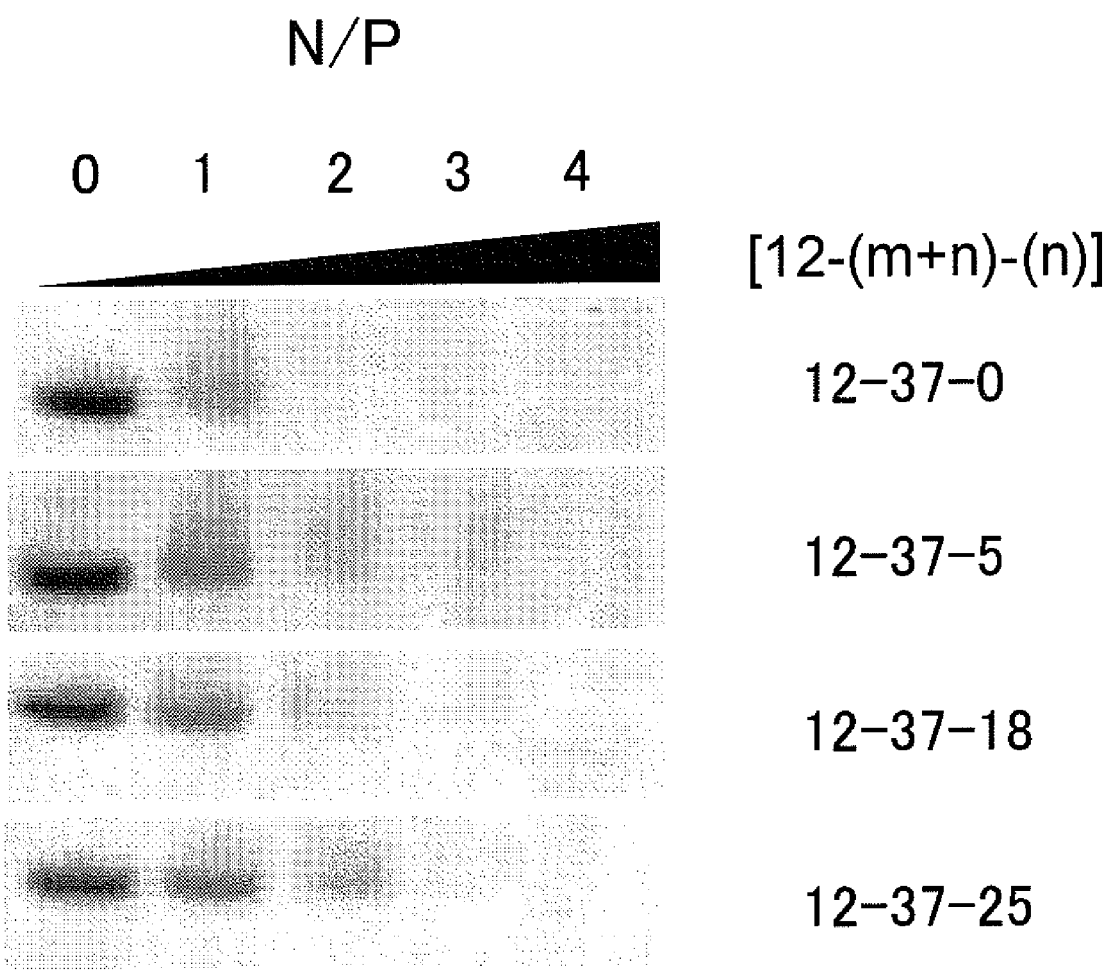
FIG. 4 shows the results of polyacrylamide gel electrophoresis of PEG-PLys (SH+)/siRNA micelle.

As a result, as the N/P ratio was increased, free siRNA became undetectable (FIG. 4). This result indicates that siRNA is included in the assembly having a large molecular weight inferred from the result in FIG. 3.

4. Particle Size Distribution of PEG-PLys (SH+)/siRNA Micelle

A treatment of forming disulfide cross-linkings was performed under conditions by which an assembly was formed by PEG-PLys(SH+) and siRNA. After the addition of 150 mM NaCl, dynamic light scattering was measured.

Figure 5:
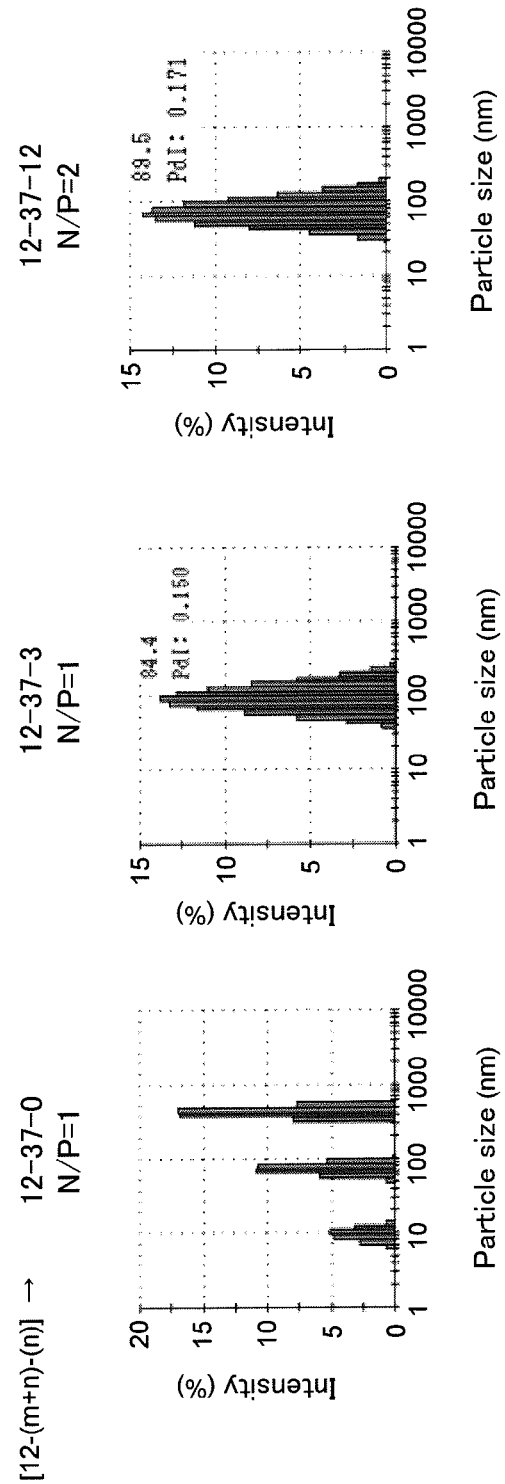
FIG. 5 shows particle size distribution of PEG-PLys (SH+)/siRNA micelle.

The assembly formed by PEG-PLys did not show monodispersity, but in the case of PEG-PLys(SH+), the size distribution in which the assembly formed by PEG-PLys(SH+) had the particle size of 90 nm or less and showed monodispersity was observed (FIG. 5).

5. Measurement of Zeta Potential of PEG-PLys (SH+)/siRNA Micelle 150 mM NaCl was added to assemblies formed by PEG-PLys(SH+) and siRNA to measure zeta potential.

Figure 6:
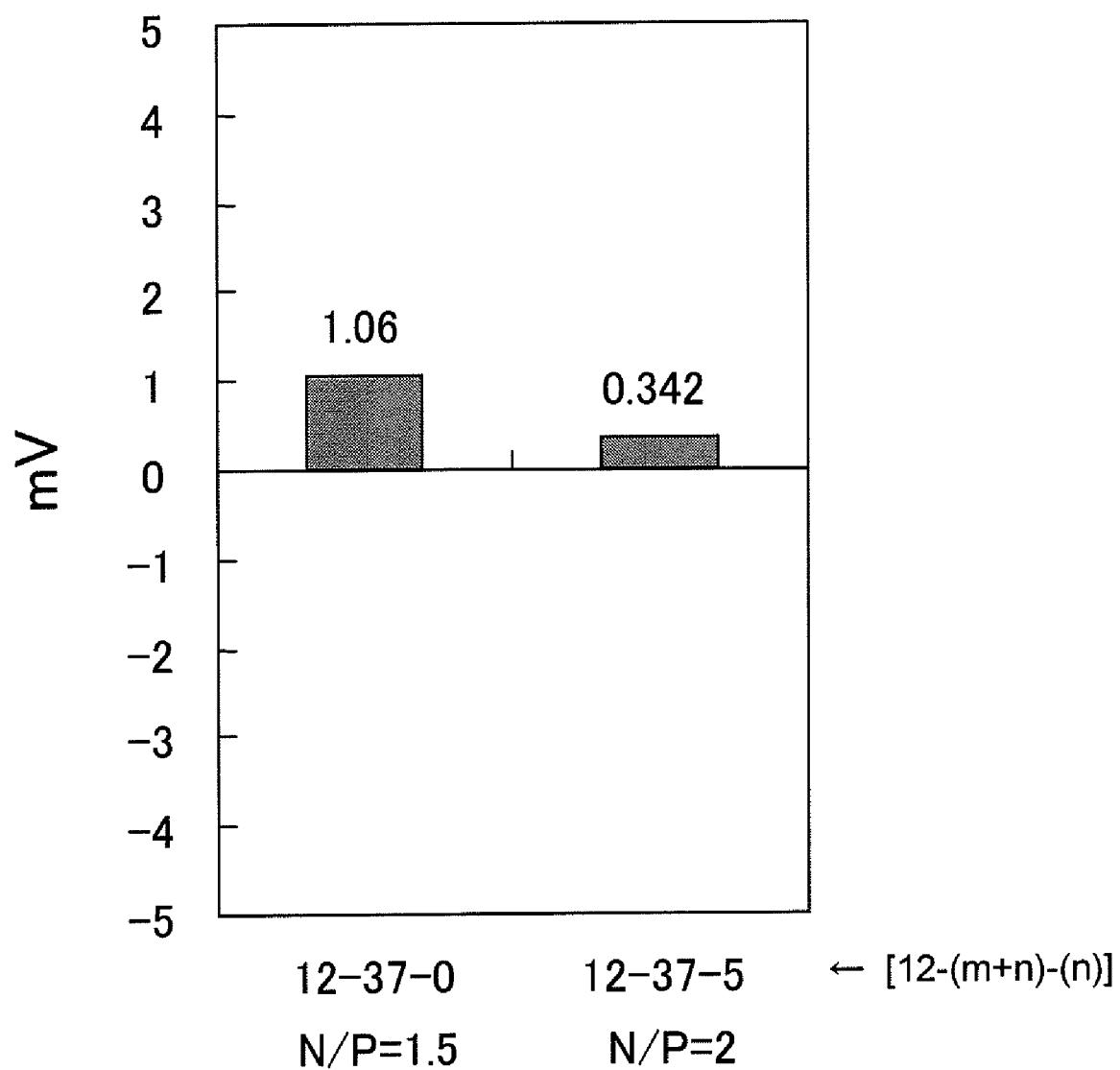
FIG. 6 shows zeta potential of PEG-PLys (SH+)/siRNA micelle.

As a result, the zeta potential of each of the assemblies was about 0 mV (FIG. 6). It is thought that a polyion complex which is formed so that its total charge becomes neutral usually loses electrostatic repulsion, thereby forming an aggregate. However, in the case of the PEG-PLys(SH+)/siRNA assembly, no aggregate was formed after allowed to stand for a long period of time, in spite of neutrality of the zeta potential.

Thus, the results shown in FIGS. 3 to 6 indicate the formation of siRNA-encapsulated polymer micelle in which the surface layer of siRNA is covered with PEG.

6. Evaluation of Stability of PEG-PLys(SH+)/siRNA Micelle

In order to examine the stabilizing effect of disulfide cross-linkings, PEG-PLys(SH+)/siRNA micelles with different ionic strengths of dispersion medium were subjected to the measurement of scattered light intensity. Usually, as the ionic strength is increased, a polyion complex becomes dissociated, and the scattered light intensity is decreased.

Figure 7:
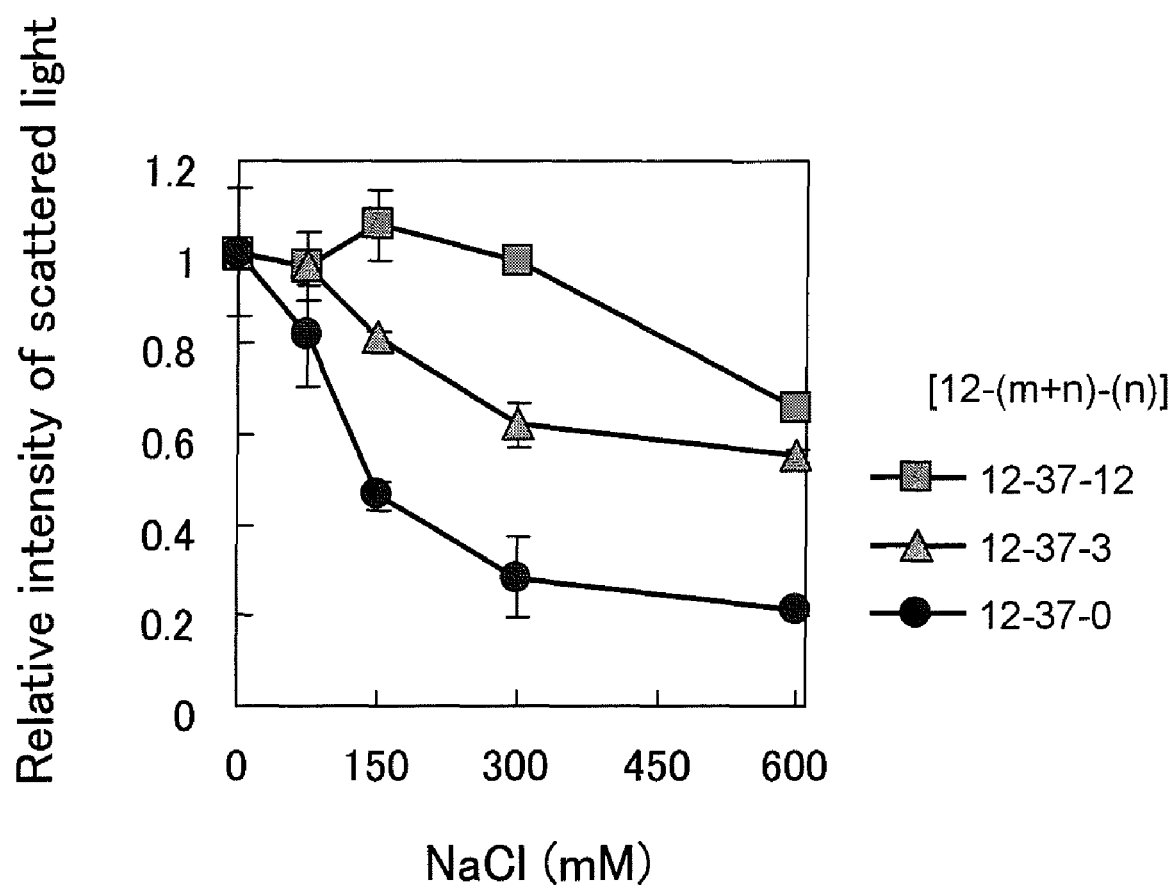
FIG. 7 is a graph showing structural stability of PEG-PLys (SH+)/siRNA micelle relative to change in ion intensity (change in NaCl concentration).

In this working example, it was observed that the PEG-PLys/siRNA assembly became dissociated as the ionic strength of dispersion medium was increased (FIG. 7). However, the PEG-PLys(SH+)/siRNA micelle was extremely stable. In particular, to the extent of about 150 mM NaCl, which is a physiological condition, the assembly showed almost no change and had high structure stability, and it was shown that the micelle is extremely suitable for practical use (FIG. 7).

7. Transfection of siRNA into Culture Cell

To the Huh7 cell (human hepatoma-derived cell) which expresses two types of luciferases (Pp-Luc and Rr-Luc), a polymer micelle in which siRNA against one of the luciferases (Pp-Luc) was encapsulated was given, thereby evaluating the effect of suppression of gene expression.

Figure 8:
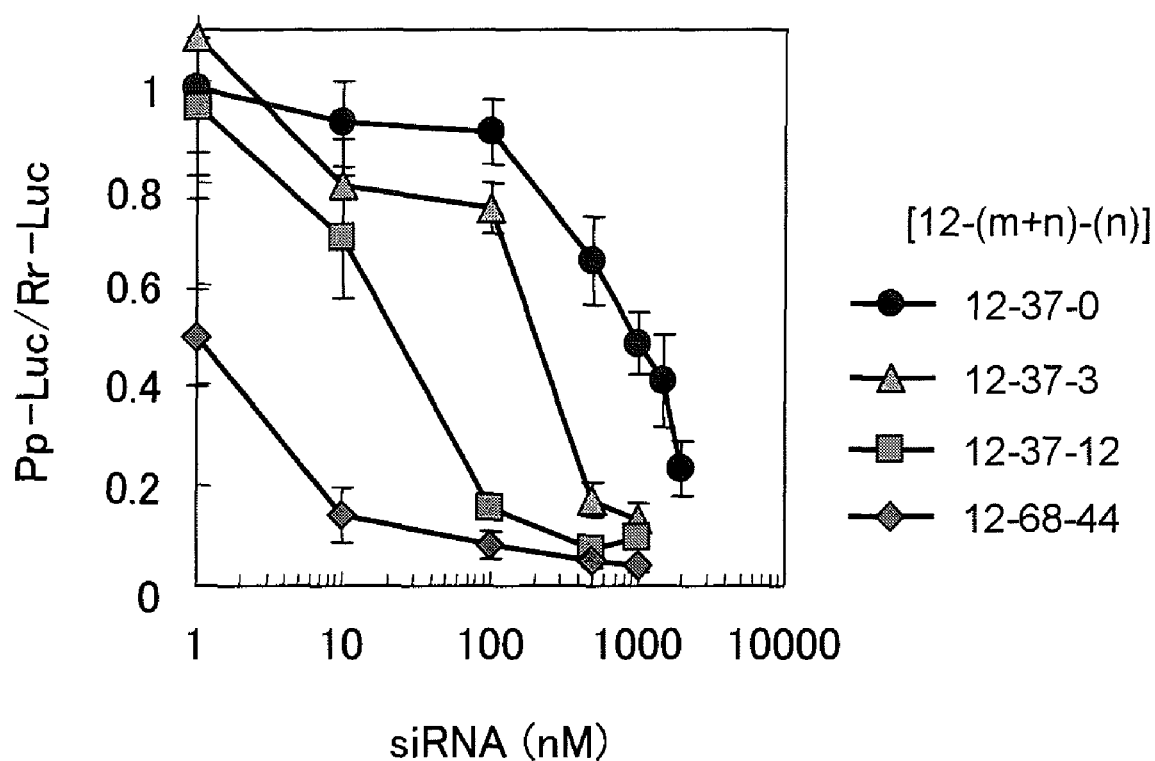
FIG. 8 is a graph showing the influence of PEG-PLys (SH+) on the transfection efficiency of siRNA into Huh7 cell.

As a result, as the efficiency of introduction of 1-imino-4-mercaptobutyl group into PEG-PLys(SH+) was increased, the effect of suppression of gene expression, i.e., the ability to deliver siRNA was remarkably improved (FIG. 8). When comparison was made at a siRNA concentration for achieving 50% knockdown, the maximum ability to deliver siRNA when using PEG-PLys(SH+) (specifically 12-68-44) was about 1000 times that when using PEG-PLys (specifically 12-37-0) (FIG. 8).

Example 2

Evaluation of Retentivity of siRNA-Encapsulated Disulfide-Cross-Linked Polymer Micelle in Blood A fluorescently-labeled siRNA (Cy3-siRNA)-encapsulated disulfide-cross-linked polymer micelle was prepared, and it was intravenously administered to a mouse via the tail vein to evaluate its retentivity in blood (stability in blood).

<Methods> siRNA similar to the siRNA used in Example 1 (double-stranded; SEQ ID NOs: 1 and 2) was fluorescently labeled with Cy3 according to the ordinary method (Cy3-siRNA). Subsequently, a disulfide-cross-linked polymer micelle in which this Cy3-siRNA was encapsulated (PEG-PLys(SH+)/Cy3-siRNA micelle) was prepared. In this regard, the micelle was prepared in a manner similar to that in Example 1. In this working example, 4 types of PEG-PLys(SH+) products, which respectively have different ratios of 1-imino-4-mercaptobutyl group introduction (ratios of substituent introduction; % substitution) of 14%, 49%, 68% and 97%, were used for preparation of micelle, thereby preparing 4 types of micelles with different degrees of cross-linkings. As controls, Cy3-siRNA (Naked siRNA: not encapsulated in a micelle), and a Cy3-siRNA-encapsulated polymer micelle, in which PEG-PLys(SH+) having the ratio of substituent introduction of 0% (i.e., PEG-PLys) was used, were prepared.

The PEG-PLys(SH+)/Cy3-siRNA micelle was intravenously administered to a mouse (Balb/c nude mouse, 8 to 10-week-old, female) via the tail vein so that the amount of siRNA per the weight of the mouse became 1 mg/kg. The aforementioned controls were similarly subjected to administration.

7.5 minutes after the administration, whole blood was collected from the inferior vena cava of the mouse, and plasma was separated therefrom by centrifugation (2000 g, 10 minutes, 4° C.). To the separated plasma, 10 mM dithiothreitol and 0.002 w/v % polyvinyl sulfate were added to destroy the disulfide-cross-linked micelle. After that, fluorescence of Cy3 (excitation wavelength: 544 nm, fluorescence wavelength: 590 nm) was measured using a fluorescence plate reader.

<Results and Discussion>

Figure 9:
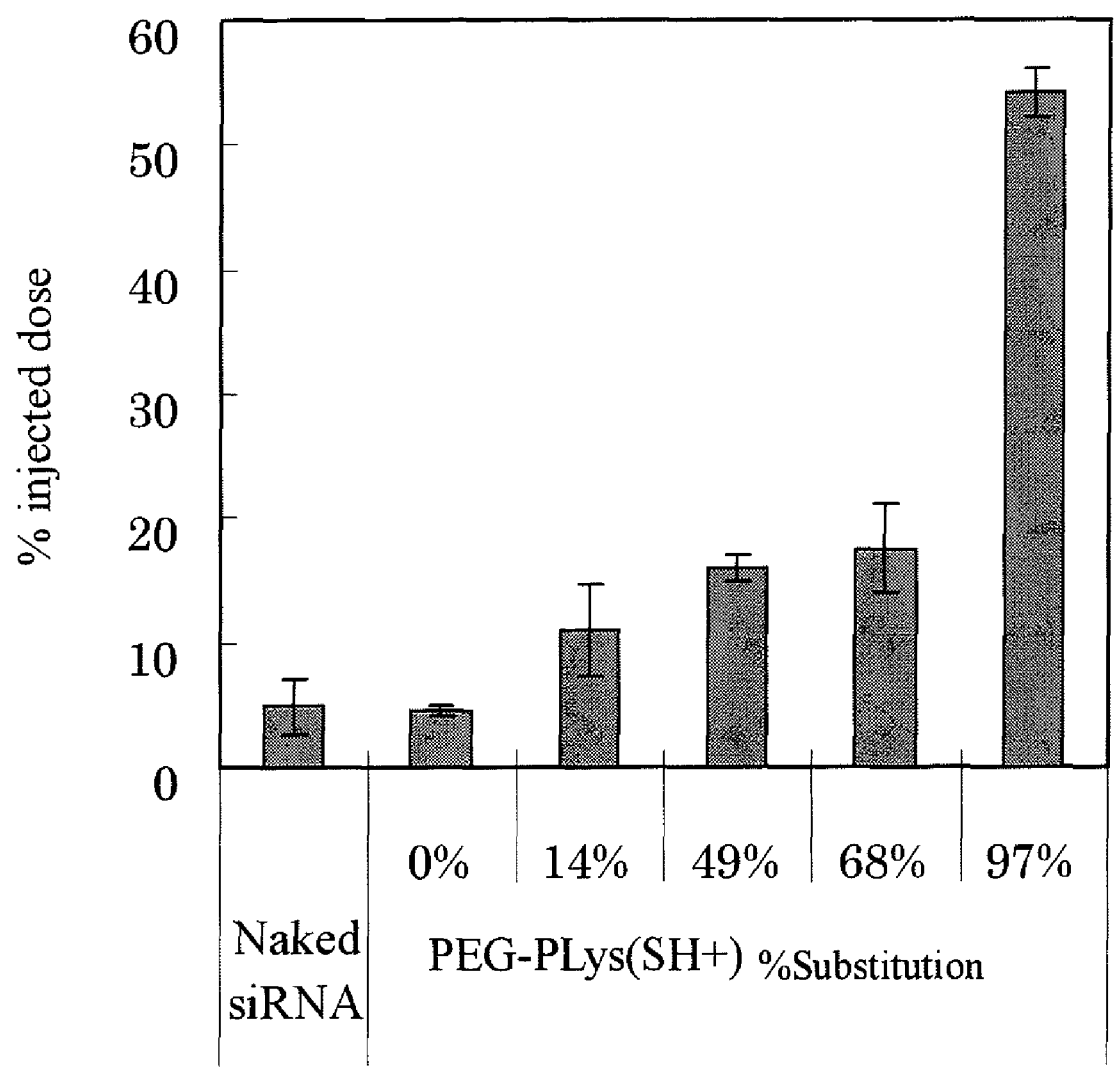
FIG. 9 is a graph showing evaluation results of retentivity of Cy3-siRNA-encapsulated disulfide-cross-linked polymer micelle in mouse blood.

As shown in FIG. 9, in the case of Naked siRNA, 95% of the injected dose was lost from the blood stream only 7.5 minutes after the administration via the tail vein. Further, when administering siRNA using the micelle without disulfide cross-linkings (the ratio of substituent introduction: 0%), there was no particular effect of improvement of retentivity in blood. On the other hand, in the case of the siRNA encapsulated in the disulfide-cross-linked polymer micelle using PEG-PLys(SH+), the improvement of retentivity in blood was recognized as the ratio of substituent introduction was increased. In particular, in the case of administration of PEG-PLys(SH+)/Cy3-siRNA micelle using PEG-PLys(SH+) having the ratio of substituent introduction of 97%, the amount lost from the blood stream was suppressed to 50% or lower.

INDUSTRIAL APPLICABILITY

According to the present invention, a siRNA-encapsulated polymer micelle complex (a polyion complex), which has high monodispersibility and structural stability and is excellent in the ability of delivering siRNA into a cell, can be provided. In addition, according to the present invention, a nucleic acid delivery device, a nucleic acid delivery kit, a pharmaceutical composition and a gene therapy agent, each of which comprises the polyion complex, can be provided.

The polyion complex of the present invention can hold siRNA, which is an easily-degradable and unstable chemical species under physiological circumstances, in an extremely stable state until it reaches a target cell. Therefore, the polyion complex of the present invention is highly suitable for practical use in the field of researches and clinical discipline such as preparation of knockout animals and gene therapy of various diseases.

In the polyion complex of the present invention, thiol groups at the terminuses of the side chains of the polycation portion are reacted with each other to form a disulfide bond, thereby further stabilizing the structure of the polyion complex. After the polyion complex is introduced (delivered) into a cell, the disulfide bond may be cleaved depending on increase in the glutathione concentration. Therefore, the polyion complex of the present invention is highly useful as a siRNA delivery device, which releases siRNA in a cell responding to the environment.

SEQUENCE LISTING FREE TEXT

SEQ ID NO: 1: DNA/RNA bound molecule
SEQ ID NO: 2: DNA/RNA bound molecule

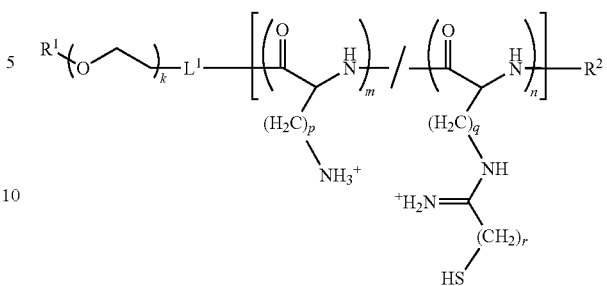

wherein each of $R^1$ and $R^2$ independently represents a hydrogen atom or a substitutable linear or branched alkyl group containing 1 to 12 carbon atoms;

$L^1$ represents NH, a group represented by formula (2):

wherein $p1$ represents an integer between 1 and 5, or $L^1$ represents a group represented by formula (3):

wherein $L^{2a}$ represents OCO, OCONH, NHCO, NHCOO, NHCONH, CONH or COO, $L^{3a}$ represents NH, and $q1$ represents an integer between 1 and 5;

k represents an integer between 100 and 500; m represents an integer between 0 and 499; n represents an integer between 1 and 500; and m+n=10 to 500; p represents an integer between 1 and 10; q represents an integer between 1 and 10; and r represents an integer between 1

---

---

The invention claimed is:

1. A micellar polyion complex, which comprises: a block copolymer constituted by a polyethylene glycol portion and a polycation portion having a side chain whose terminus is a thiol group; wherein the block copolymer is represented by formula (1): and 10, wherein the symbol "/" in formula (1) indicates that the sequence order of respective monomer units described at the left and right sides thereof (the number of units: m+n) is arbitrarily determined and wherein n/(m+n) is greater than or equal to 0.65 and less than or equal to 1; and siRNA.

2. The polyion complex according to claim 1, wherein the polycation portion and siRNA bind to each other by electrostatic interaction.

3. The polyion complex according to claim 1, wherein the polycation portion and siRNA form a core portion, and the polyethylene glycol portion forms a shell portion around the core portion.

4. The polyion complex according to claim 1, wherein an intramolecular and/or intermolecular disulfide bond is formed in the block copolymer.

5. A device for delivering a nucleic acid into a cell, which comprises the polyion complex according to claim 1.

6. A kit for delivering a nucleic acid into a cell, which comprises a block copolymer constituted by a polyethylene glycol portion and a polycation portion having a side chain whose terminus is a thiol group; wherein the block copolymer is represented by formula (1):

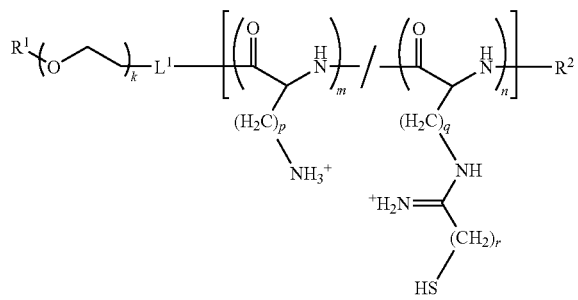
(1)

wherein each of $R^1$ and $R^2$ independently represents a hydrogen atom or a substitutable linear or branched alkyl group containing 1 to 12 carbon atoms;

$L^1$ represents NH, a group represented by the following general formula (2):

$$-(CH_2)_{p1}-NH-\qquad(2)$$

wherein $p1$ represents an integer between 1 and 5, or $L^1$ represents a group represented by formula (3):

$$-L^{2a}-(CH_2)_{q1}-L^{3a}-\qquad(3)$$

wherein $L^{2a}$ represents OCO, OCONH, NHCO, NHCOO, NHCONH, CONH or COO, $L^{3a}$ represents NH, and $q1$ represents an integer between 1 and 5;

k represents an integer between 100 and 500; m represents an integer between 0 and 499; n represents an integer between 1 and 500; and m+n=10 to 500; p represents an integer between 1 and 10; q represents an integer between 1 and 10; and r represents an integer between 1 and 10, wherein the symbol "/" in formula (1) indicates that the sequence order of respective monomer units described at the left and right sides thereof (the number of units: m+n) is arbitrarily determined and wherein n/(m+n) is greater than or equal to 0.65 and less than or equal to 1.

7. A kit for delivering a nucleic acid into a cell, which comprises the polyion complex according to claim 1.

8. A pharmaceutical composition for treating cancer, which comprises the polyion complex according to claim 1.

9. A gene therapy agent for cancer, which comprises the composition according to claim 8 as an active ingredient.

10. The polyion complex according to claim 1 wherein n/(m+n) is greater than or equal to 0.70 and less than or equal to 1.

11. The polyion complex according to claim 1 wherein n/(m+n) is greater than or equal to 0.97 and less than or equal to 1.

12. The polyion complex according to claim 1 wherein the size of the complex is between 30 and 150 nm.

* * * * *